(12) United States Patent
McNeil

(10) Patent No.: US 9,744,277 B2
(45) Date of Patent: *Aug. 29, 2017

(54) LIMITED-ACCESS, REDUCED-PRESSURE SYSTEMS AND METHODS

(71) Applicant: KCI Licensing, Inc., San Antonio, TX (US)

(72) Inventor: Bruce McNeil, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 245 days.

This patent is subject to a terminal disclaimer.

(21) Appl. No.: 14/045,946

(22) Filed: Oct. 4, 2013

(65) Prior Publication Data

US 2014/0039425 A1  Feb. 6, 2014

Related U.S. Application Data

(60) Continuation of application No. 13/348,306, filed on Jan. 11, 2012, now Pat. No. 8,575,416, which is a
(Continued)

(51) Int. Cl.
*A61F 13/00* (2006.01)
*A61M 1/00* (2006.01)

(52) U.S. Cl.
CPC ................................ *A61M 1/0088* (2013.01)

(58) Field of Classification Search
CPC .. A61M 1/0088; A61M 1/0084; A61M 1/008; A61M 27/00; A61L 15/26; A61L 15/425
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Kim M Lewis

(57) ABSTRACT

A reduced-pressure treatment system for applying reduced pressure to a tissue site at a limited-access location on a patient includes a reduced-pressure source, a treatment manifold for placing proximate the tissue site and operable to distribute reduced pressure to the tissue site, and a sealing member for placing over the tissue site and operable to form a pneumatic seal over the tissue site. The reduced-pressure treatment system also includes a reduced-pressure bridge and a moisture-removing device on at least portion of the reduced-pressure bridge. The reduced pressure bridge includes a delivery manifold operable to transfer the reduced pressure to the treatment manifold, an encapsulating envelope at least partially enclosing the delivery manifold and having a patient-facing side, and a reduced-pressure-interface site formed proximate one end of the reduced-pressure bridge.

27 Claims, 8 Drawing Sheets

Related U.S. Application Data division of application No. 12/403,296, filed on Mar. 12, 2009, now Pat. No. 8,158,844.

(60) Provisional application No. 61/103,566, filed on Oct. 8, 2008.

(58) Field of Classification Search
USPC .... 604/313, 289, 290, 315–317; 602/41, 42, 602/46, 51–53
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A * | 1/1993 | Svedman et al. ............. 604/305 |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,381,859 B2 * | 6/2008 | Hunt et al. ....................... 602/46 |
| 8,158,844 B2 * | 4/2012 | McNeil ........................... 602/42 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0030304 A1 * | 2/2004 | Hunt et al. .................... 604/317 |
| 2006/0079852 A1 | 4/2006 | Bubb et al. | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treat-

(56) References Cited

OTHER PUBLICATIONS ment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hyperemia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

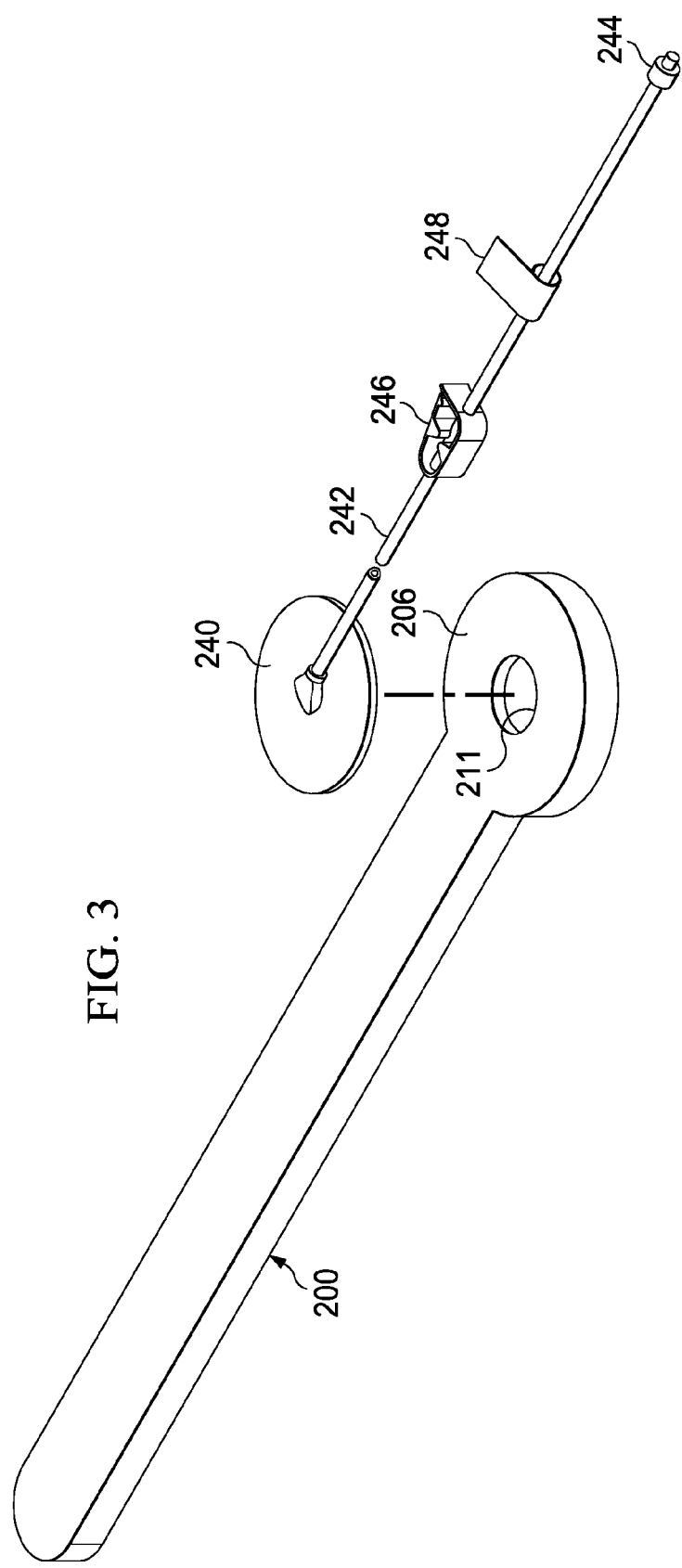

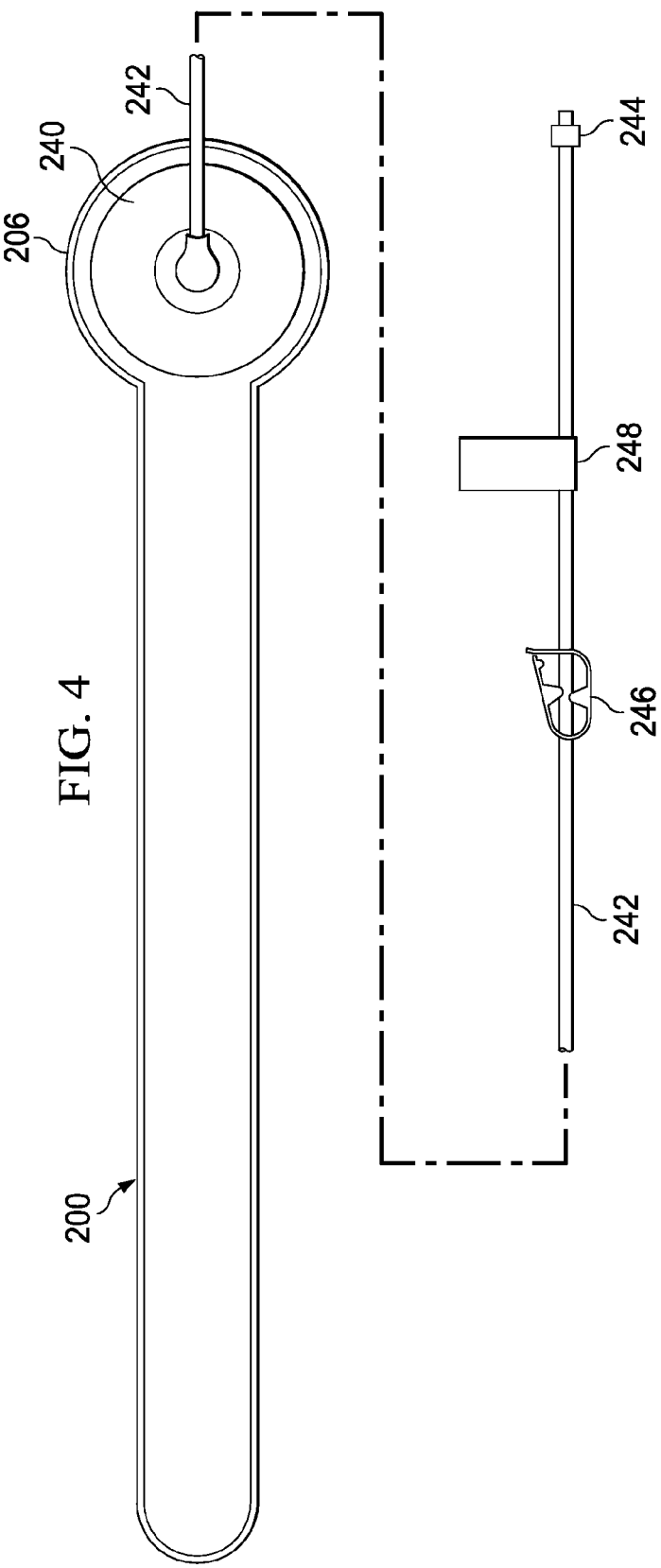

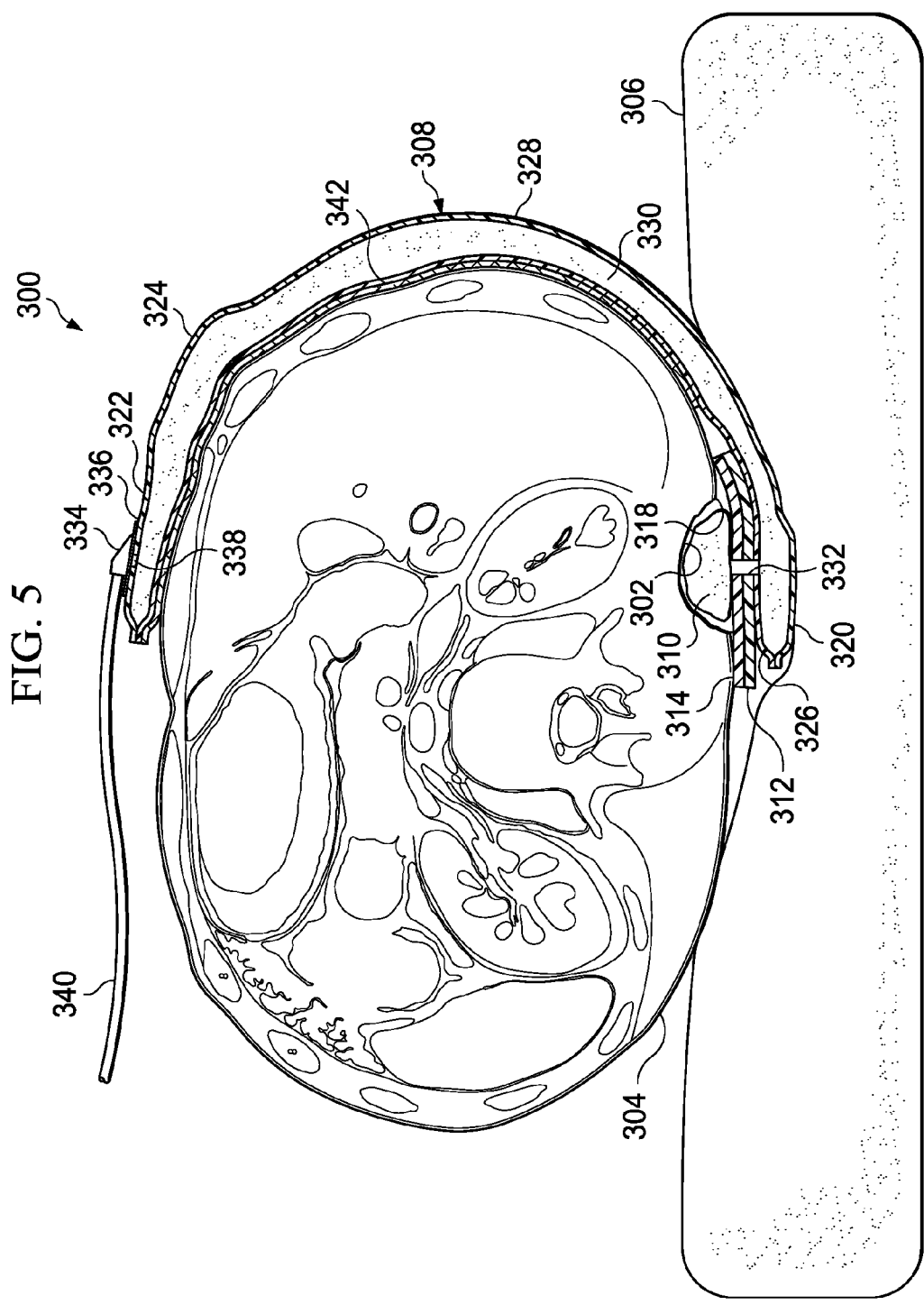

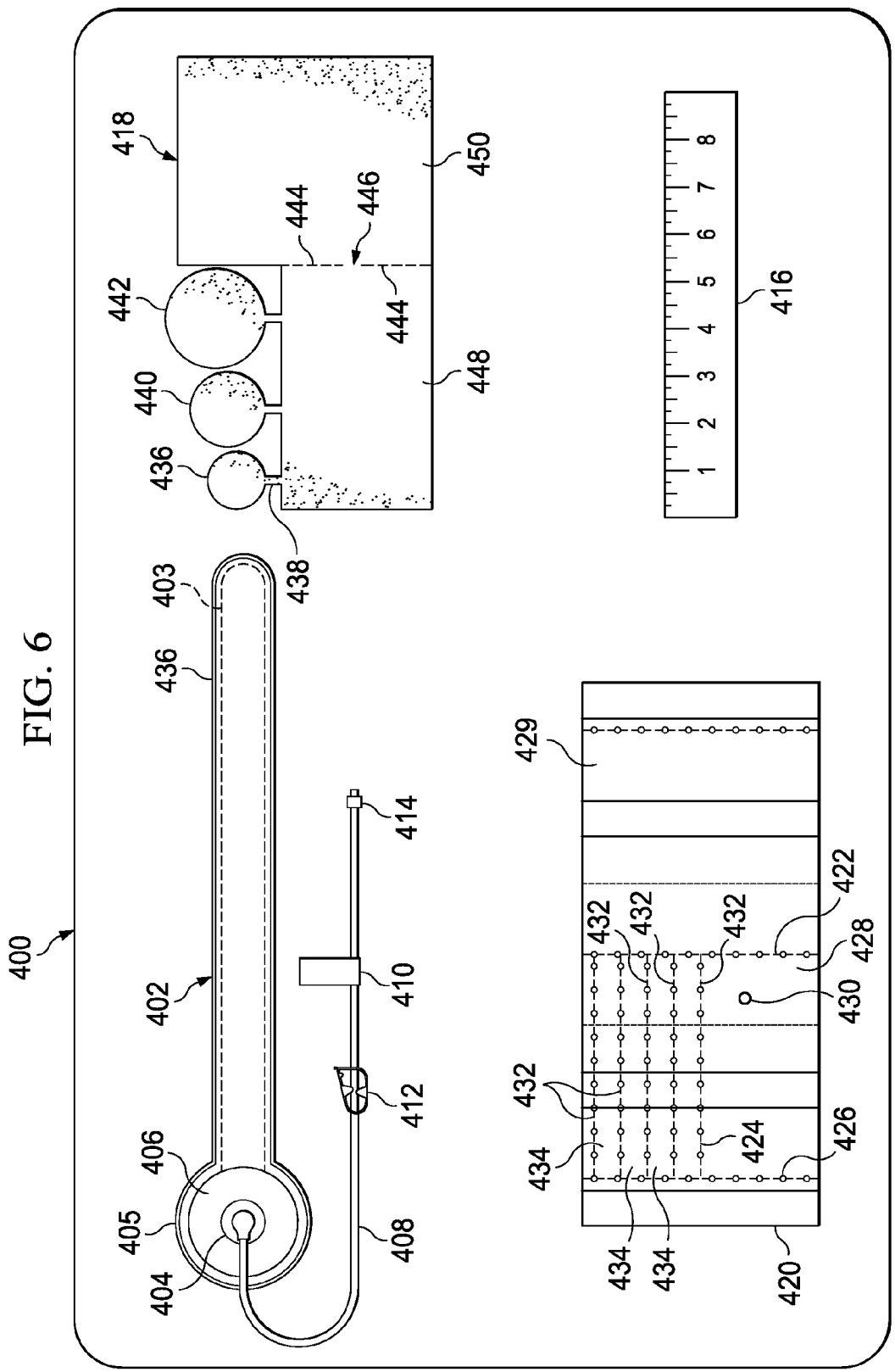

LIMITED-ACCESS, REDUCED-PRESSURE SYSTEMS AND METHODS

RELATED APPLICATIONS

This application is a continuation of U.S. patent application Ser. No. 13/348,306, filed Jan. 11, 2012, which is a divisional application of U.S. patent application Ser. No. 12/403,296, filed Mar. 12, 2009, entitled "Limited-Access, Reduced Pressure Systems and Methods", which claims the benefit under 35 USC §119(e) of the filing of U.S. Provisional Patent Application No. 61/103,566, filed Oct. 8, 2008, entitled "System and Method for Applying Reduced Pressure to a Patient's Limb, Such As a Foot." The entire contents of each of the applications referenced above are incorporated herein by reference for all purposes.

BACKGROUND

The present invention relates generally to medical treatment systems and, more particularly, but not by way of limitation, to limited-access, reduced-pressure systems and methods.

Clinical studies and practices have shown that providing reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Unless otherwise indicated, as used herein, "or" does not require mutual exclusivity.

Providing reduced pressure to limited-access locations has been difficult. One example of a difficult limited-access location is the bottom sole (plantar) of a patient's foot or other anatomical locations that are difficult to service. A related illustrative example of a limited-access location is inside an offloading device, such as a walking boot or removable walker. Another example of a limited-access location is a tissue site on a bed-ridden patient's back. Other illustrative examples include a tissue site under a compression garment and sacral wounds on the foot.

SUMMARY

Problems with existing reduced-pressure treatment devices and systems are addressed by the systems, apparatus, and methods of the illustrative embodiments described herein. According to an illustrative embodiment, a reduced-pressure treatment system for applying reduced pressure to a tissue site at a limited-access location on a patient includes a reduced-pressure source, a treatment manifold for placing proximate the tissue site and operable to distribute reduced pressure to the tissue site, and a sealing member for placing over the tissue site and operable to form a pneumatic seal over the tissue site. The reduced-pressure treatment system also includes a reduced-pressure bridge that includes a delivery manifold operable to transfer the reduced pressure to the treatment manifold, an encapsulating envelope at least partially enclosing the delivery manifold and having a patient-facing side, a reduced-pressure-interface site formed proximate one end of the reduced-pressure bridge. The reduced-pressure treatment system also includes a moisture-removing device.

According to another illustrative embodiment, a reduced-pressure bridge for delivering reduced pressure to a reduced-pressure dressing from a remote site includes a delivery manifold operable to transfer a reduced pressure and an encapsulating envelope at least partially enclosing the delivery manifold and having a patient-facing side. A reduced-pressure-interface site is formed proximate a second end of the reduced-pressure bridge. The encapsulating envelope has a second aperture formed on the patient-facing side of the encapsulating envelope. The reduced-pressure bridge also includes a moisture-removing device on at least a portion of the encapsulating envelope.

According to another illustrative embodiment, a method for delivering reduced pressure to a tissue site at a limited-access location includes the steps of: disposing a first manifold proximate the wound and disposing a sealing member over the first manifold. The sealing member has a first aperture. The method for delivering reduced pressure to a tissue site further includes providing a reduced-pressure bridge having a first end and a second end. The reduced-pressure bridge has a second aperture proximate the first end, a moisture-removing device, and a second manifold. The method for delivering reduced pressure to a tissue site further includes coupling a reduced-pressure interface to the second end of the reduced-pressure bridge; disposing the first end of the reduced-pressure bridge over at least a portion of the sealing member with the second aperture substantially aligned with the first aperture. The first manifold may be at least partially encapsulated with an encapsulating envelope that has a patient-facing side. The method for delivering reduced pressure to a tissue site may further include fluidly coupling a reduced-pressure source to the reduced-pressure interface.

According to another illustrative embodiment, a reduced-pressure treatment kit includes a reduced-pressure bridge, the reduced-pressure bridge, a reduced-pressure interface, a reduced-pressure delivery conduit, a manifold unit, and a perforated sealing sheet. The manifold unit has a plurality of preformed treatment manifolds. The perforated sealing sheet is operable to be torn into a plurality of securing strips and a sealing member.

Other objects, features, and advantages of the illustrative embodiments will become apparent with reference to the drawings and detailed description that follow.

BRIEF DESCRIPTION OF THE DRAWINGS

FIG. 3 is schematic, perspective view showing an illustrative reduced-pressure bridge being coupled with a reduced-pressure interface;

FIG. 4 is a schematic, plan view of the reduced-pressure bridge of FIG. 3 with the reduced-pressure interface installed;

FIG. 5 is a schematic diagram of an illustrative reduced-pressure treatment system utilizing a reduced-pressure bridge shown on a traverse section through an abdomen of a patient on a bed;

FIG. 6 is a schematic diagram of an illustrative embodiment of a reduced-pressure treatment kit for use with limited-access tissue sites;

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
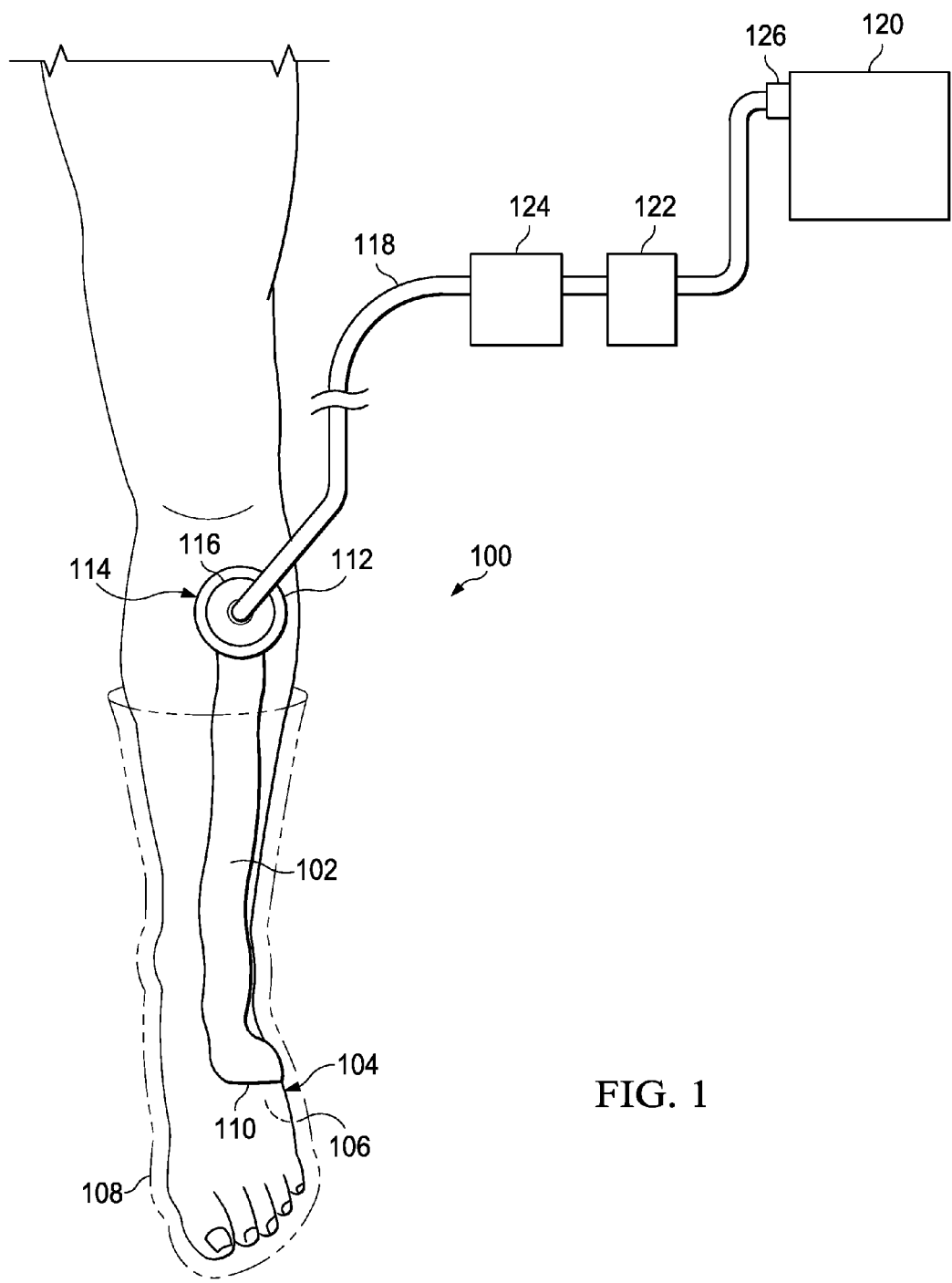
FIG. 1 is a schematic, perspective view with a portion shown as a block diagram of an illustrative reduced-pressure treatment system utilizing a reduced-pressure bridge.

Referring to FIG. 1, an illustrative embodiment of a reduced-pressure treatment system 100 is presented. The reduced-pressure treatment system 100 has an illustrative embodiment of a reduced-pressure bridge 102. The reduced-pressure bridge 102 facilitates reduced-pressure treatment of a tissue site 104 and in particular a limited-access tissue site, which in this illustration is on the bottom sole (plantar) of a patient's foot 106 and also within an offloading device, e.g., offloading boot 108 (shown in hidden lines). The reduced-pressure treatment system 100 may be used with a tissue site at a non-limited-access site or a limited-access site. Other illustrative examples of limited-access tissue sites include on a patient's back, under a compression garment, in a total contact casting (TCC), in a removable walker, in a healing sandal, in a half shoe, in an ankle foot orthoses, etc. The reduced-pressure treatment system 100 may be used with the bodily tissue of any human, animal, or other organism, including bone tissue, adipose tissue, muscle tissue, dermal tissue, vascular tissue, connective tissue, cartilage, tendons, ligaments, or any other tissue.

The reduced-pressure bridge 102 provides a low profile source of reduced pressure to be supplied to the limited-access tissue site 104 and thereby may increase patient comfort and enhance reliability of the reduced-pressure supply to the limited-access tissue site 104. Because of the low profile of the reduced-pressure bridge 102, the reduced-pressure bridge 102 may readily be used with an offloading device. As such, the reduced-pressure bridge 102 may allow the patient the benefit of both reduced-pressure treatment as well as the offloading of physical pressure. As described further below, the reduced-pressure bridge 102 may include a moisture-removing device, e.g., moisture-removing device 216 in FIG. 2B, that helps to avoid maceration of a patient's skin by removing moisture from the patient's skin.

The reduced-pressure bridge 102 has a first end 110 that is placed proximate the limited-access tissue site 104 and a second end 112. The second end 112 has a reduced-pressure-interface site 114 that is for receiving a reduced-pressure interface 116, which may be a port, such as a TRAC Pad® interface or a SensaT.R.A.C.™ pad interface from Kinetic Concepts, Inc. of San Antonio, Tex. The second end 112 is typically placed at a location on or near the patient that provides convenient access by the healthcare provider, such as a convenient location for applying reduced-pressure to the reduced-pressure-interface site 114. When an offloading device, e.g., offloading boot 108, is utilized, the reduced-pressure bridge 102 would extend from the tissue site to a place outside of the offloading device. The actual length (L) of the reduced-pressure bridge 102 may be varied to support use with a particular offloading device or application.

A reduced-pressure delivery conduit 118 may fluidly couple the reduced-pressure interface 116 to a reduced-pressure source 120. The reduced-pressure source 120 may be any device or means for supplying a reduced pressure, such as a vacuum pump or wall suction. While the amount and nature of reduced pressure applied to a site will vary according to the application, the reduced pressure will typically be between −5 mm Hg and −500 mm Hg or more typically between −25 mm Hg to −200 mm Hg. For vertical applications of the reduced-pressure bridge 102, such as is shown in FIG. 1 on an ambulatory patient's leg, a specified minimum reduced pressure may be necessary to ensure proper fluid flow. For example in one embodiment, a reduced pressure of at least −125 mm Hg has been suggested as a minimum, but other pressures may be suitable for different situations. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure. In one illustrative embodiment, a V.A.C.® Therapy Unit by Kinetic Concepts, Inc. of San Antonio may be used as the reduced-pressure source 120.

Depending on the application, a plurality of devices may be fluidly coupled to the reduced-pressure delivery conduit 118. For example, a fluid canister 122 or a representative device 124 may be included. The representative device 124 may be another fluid reservoir or canister to hold exudates and other fluids removed. Other examples of device 124 that may be included on the reduced-pressure delivery conduit 118 include the following non-limiting examples: a pressure-feedback device, a volume detection system, a blood detection system, an infection detection system, a flow monitoring system, a temperature monitoring system, a filter, etc. Some of these devices may be formed integral to the reduced-pressure source 120. For example, a reduced-pressure port 126 on the reduced-pressure source 120 may include a filter member that includes one or more filters, e.g., an odor filter.

Figure 2A:
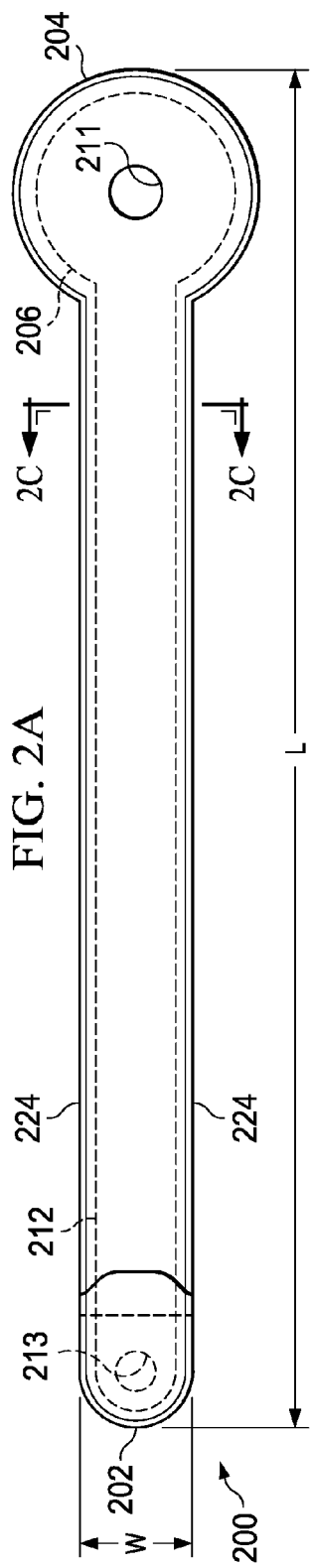
FIG. 2A is schematic, plan view of an illustrative reduced-pressure bridge.
Figure 2B:
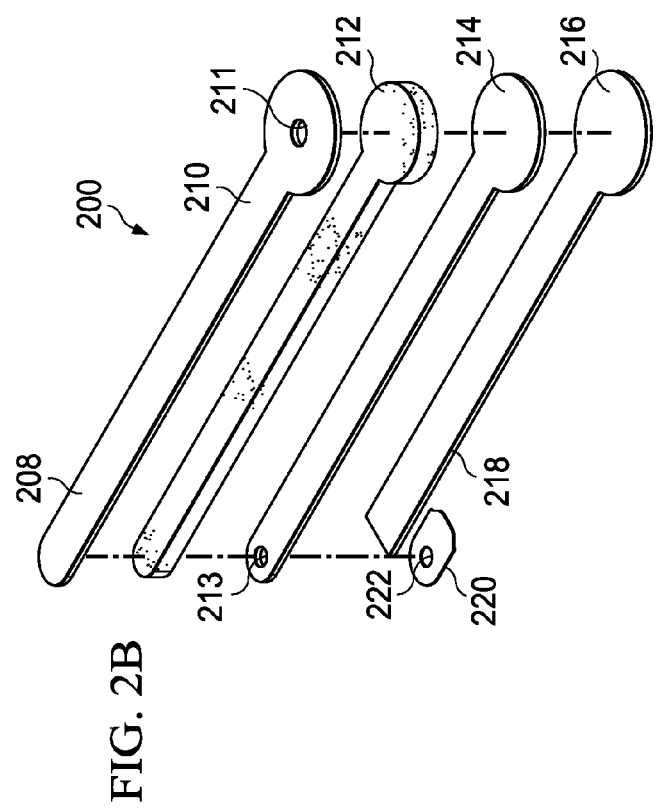
FIG. 2B is a schematic, perspective, exploded view of the illustrative reduced-pressure bridge of FIG. 2A.
Figure 2C:
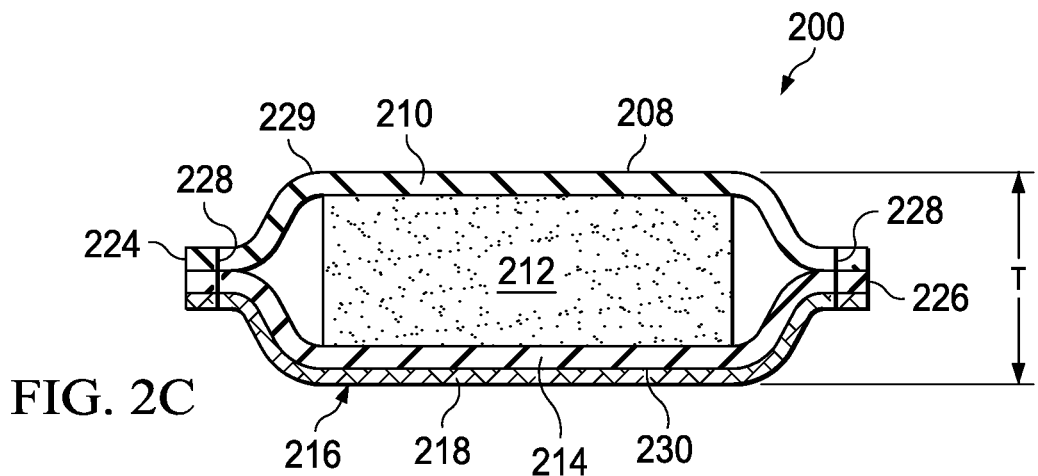
FIG. 2C is a schematic, cross-sectional view taken along line 2C-2C of the illustrative reduced-pressure bridge of FIG. 2A.

Referring now to FIGS. 2A-2C, an illustrative, reduced-pressure bridge 200 will be presented. The illustrative, reduced-pressure bridge 200 has a first end 202 and a second end 204. The first end 202 of the illustrative, reduced-pressure bridge 200 is configured to provide reduced pressure to a first manifold, or treatment manifold (e.g., treatment manifold 310 in FIG. 5) and the second end 204 has a reduced-pressure-interface site 206.

Referring primarily to FIG. 2B, the layers that make up the illustrative, reduced-pressure bridge 200 are presented. A first encapsulating member 210 is on a first side 208 of the illustrative, reduced-pressure bridge 200. The first encapsulating member 210 may have an aperture 211 formed proximate the second end 204. A second manifold, or delivery manifold 212, is disposed proximate the first encapsulating member 210. A second encapsulating member 214 is disposed proximate a second side of the delivery manifold 212. The second encapsulating member 214 may be formed with an aperture 213 proximate the first end 202. A moisture-removing device 216 is disposed proximate the second encapsulating member 214, which in this illustrative embodiment is a wicking layer 218. A releasable backing member or release liner 220 may be included on the first end 202 to releasably cover an adhesive as is explained further below. The releasable backing member 220 may be formed with an aperture 222 that aligns with the aperture 213 in the second encapsulating member 214.

The delivery manifold 212 may be any material capable of transferring reduced pressure. In one embodiment, the delivery manifold 212 is a foam material, such as a Granu-Foam® material from Kinetic Concepts, Inc. of San Antonio, Tex. The delivery manifold 212 may be formed from the same material as a treatment manifold (e.g., treatment manifold 310 in FIG. 5). The delivery manifold 212 may have any thickness, such as a thickness in the range of 3-20 millimeters, 5-10 millimeters, 6-7 millimeters, etc. The thickness of the delivery manifold 212 may be varied to minimize or eliminate pressure points on the tissue site. The thickness of the delivery manifold 212 may also be selected to support fluid removal from the tissue site and transfer into a canister (e.g., fluid canister 122 in FIG. 1).

The first encapsulating member 210 and the second encapsulating member 214 may be composed of any material that facilitates maintaining reduced pressure within a first encapsulating envelope 229 formed from the first encapsulating member 210 and the second encapsulating member 214. In one embodiment, the first encapsulating member 210 and the second encapsulating member 214 include a polyurethane film, but any suitable drape material may be readily used, such as any natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, silicones, 3M Tegaderm® drape material, or acrylic drape material, such as one available from Avery. These are non-limiting examples.

Referring now primarily to FIGS. 2A and 2C, a periphery portion 224 of the first encapsulating member 210 and a periphery portion 226 of the second encapsulating member 214 may be coupled, such as by RF weld 228, to form the first encapsulating envelope 229. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, mechanical, or thermal coupling. Fluid coupling means that fluid is in communication between the designated parts or locations. The first encapsulating member 210 and the second encapsulating member 214 may be coupled using any technique, including without limitation welding (e.g., ultrasonic or RF welding), bonding, adhesives, cements, etc. The first encapsulating envelope 229 may completely enclose the delivery manifold 212. The moisture-removing device 216 may be coupled to at least a portion of the first encapsulating envelope 229 using any technique. The wicking layer may be coupled to a patient-facing side 230 of the second encapsulating member 214 of the first encapsulating envelope 229.

The moisture-removing device 216 pulls moisture, e.g., perspiration, away from a patient's skin and thereby helps to avoid maceration of the patient's skin and enhances comfort. The extent of the wicking layer 218 can be varied both laterally (width) and longitudinally (lengthwise). For example, the wicking layer 218 may cover 100 percent or more than 90 percent, 80 percent, 70 percent, 60 percent, or 50 percent of the patient-facing second encapsulating member 24. The wicking layer 218 pulls moisture to a place where the moisture can evaporate more readily. In the illustrative embodiment of FIGS. 2A-2C, the moisture removing device 216 is the wicking layer 218. For example, the wicking layer 218 may be a cloth-material drape, a non-woven fabric, a knitted polyester woven textile material, such as the one sold under the name InterDry® AG material from Coloplast A/S of Denmark, GORTEX® material, DuPont Softesse® material, etc.

Figure 2D:
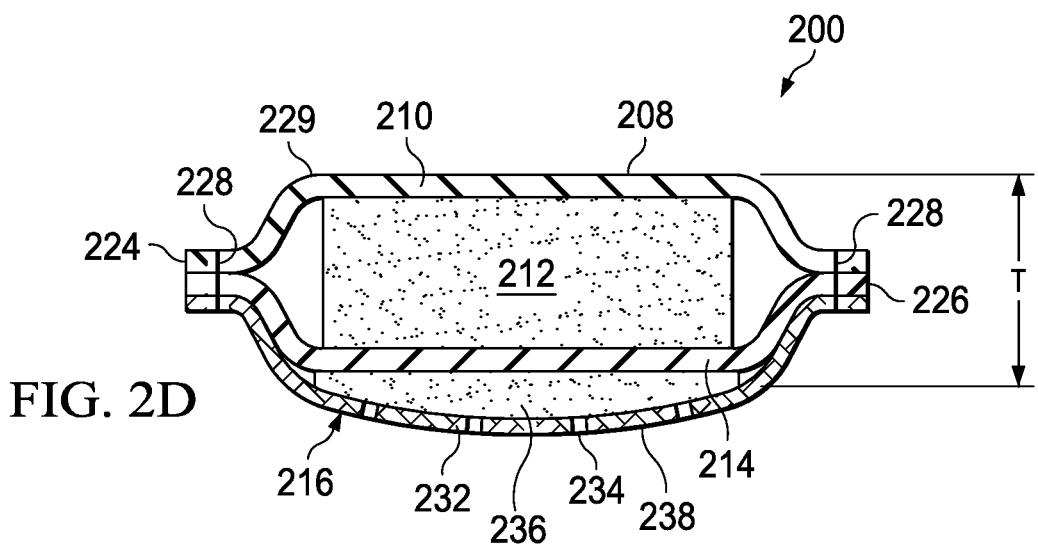
FIG. 2D is a schematic, cross-sectional view of an alternative illustrative reduced-pressure bridge.

Referring now to FIG. 2D, an alternative embodiment of the moisture-removing device 216 is presented. In this embodiment, a third encapsulating member 232 is provided with a plurality of apertures or fenestrations 234. The third encapsulating member 232 covers all or at least a portion of a third manifold 236, or comfort manifold. A periphery portion of the third encapsulating member 232 is also coupled by any technique, such as by RF weld 228. In conjunction with the second encapsulation member 214, the third encapsulation member 232 forms a second encapsulating envelope 238. In operation, a reduced pressure is supplied within the second encapsulation member 214 and any fluid against a patient's skin is pulled through the plurality of apertures 234 into the third manifold 236 and delivered elsewhere, e.g., to a canister, for storage or disposal.

In still another alternative embodiment of the moisture-removal device 216, a moisture vapor permeable material is pneumatically coupled to a negative pressure source to provide active removal adjacent the illustrative, reduced-pressure bridge 200. In still another illustrative embodiment, apertures may be formed on the second encapsulating member 214 that allow the reduced pressure in the first encapsulating envelope 229 to pull fluids into the delivery manifold 212. In still another illustrative embodiment of a moisture-removing device, apertures may be formed in the second encapsulating member 214 that allow the reduced pressure in the first encapsulating envelope 229 to pull fluids into the delivery manifold 212, and reduced-pressure valves may be associated with the apertures that close when reduced pressure is absent.

Referring again primarily to FIGS. 2A-2C, the illustrative, reduced-pressure bridge 200 has a length (L), a width (W), and a thickness (T). The illustrative, reduced-pressure bridge 200 preferably has a low of profile, e.g., small dimension T, as possible. For non-limiting examples, T may be 30 mm, 20 mm, 15 mm, 10 mm, 5 mm, or less. In other embodiments, T may take any size. Moreover, the comfort or function of the illustrative, reduced-pressure bridge 200 may be enhanced by using a length (L) to width (W) ratio that involves having the length dimension greater than the width. For example, in one embodiment, the relationship is L>2 W. In another illustrative embodiment, the relationship is L>6 W. In another illustrative embodiment, the relationship is L>12 W. In another illustrative embodiment, the relationship is L>15 W. In one illustrative embodiment, L is approximately 668 mm and W is approximately 56 mm.

Referring now to FIG. 3, the illustrative reduced-pressure bridge 200 is shown with a reduced-pressure interface 240 about to be coupled to the reduced-pressure-interface site 206 of the illustrative, reduced-pressure bridge 200. The aperture 211 in the first encapsulating member 210 substantially aligns with a central portion of the reduced-pressure interface 240 to provide a fluid coupling. A reduced-pressure delivery conduit 242 is coupled at one end to the reduced-pressure interface 240 and at the other end has a fitting 244 that facilitates coupling to a reduced-pressure source (not shown). A restricting clip or clamp 246 and a visual indicia flag 248 may also be included on a portion of the reduced-pressure delivery conduit 242. FIG. 4 shows a plan view with the reduced-pressure interface 240 coupled to the reduced-pressure-interface site 206.

Referring now to FIG. 5, a reduced-pressure treatment system 300 is presented. The reduced-pressure treatment system 300 is shown deployed to treat a tissue site 302 on a patient's back 304. If the patient is bed-ridden, the patient's back 304 may be pressed against a portion of a bed 306. In such a situation, the use of a reduced-pressure bridge 308, or transfer member, as part of the reduced-pressure treatment system 300 may be particularly beneficial to the patient. The reduced-pressure bridge 308 is analogous to the illustrative, reduced-pressure bridge 200 presented above.

A treatment manifold 310 is disposed proximate the tissue site 302. A sealing member 312 having an attachment device 314 on a patient-facing side is disposed over the treatment manifold 310. The term "manifold" as used herein generally refers to a substance or structure that helps to distribute reduced-pressure and to transport fluids. The treatment manifold 310 typically includes a plurality of flow channels or pathways that are interconnected to improve distribution of fluids provided to and removed from the tissue site 302 around the treatment manifold 310. The treatment manifold 310 may be a biocompatible material that is capable of being placed in contact with the tissue site 302 and distributing reduced pressure to the tissue site 302. Examples of treatment manifolds 310 may include, for example, without limitation, devices that have structural elements arranged to form flow channels, such as, for example, cellular foam, open-cell foam, porous tissue collections, liquids, gels, and foams that include, or cure to include, flow channels. The treatment manifold 310 may be porous and may be made from foam, gauze, felted mat, or any other material suited to a particular biological application. In one embodiment, the treatment manifold 310 is a porous foam and includes a plurality of interconnected cells or pores that act as flow channels. The porous foam may be a polyurethane, open-cell, reticulated foam, such as a GranuFoam® material manufactured by Kinetic Concepts, Incorporated of San Antonio, Tex. In some situations, the treatment manifold 310 may also be used to distribute fluids, such as medications, antibacterials, growth factors, and various solutions to the tissue site 302.

The attachment device 314 may be used to hold the sealing member 312 against the patient's epidermis or another layer, such as a gasket or additional sealing member. The attachment device 314 may take numerous forms, e.g., a medically acceptable, pressure-sensitive adhesive, cement, hydrocolloid, etc.

The sealing member 312 and the attachment device 314 are formed with a first aperture 318. The sealing member 312 may be any material that provides a pneumatic seal. The sealing member may, for example, be an impermeable or semi-permeable, elastomeric material that has pore sizes less than about 20 microns. "Elastomeric" means having the properties of an elastomer. Elastomeric material, or elastomers, generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of sealing member materials include a silicone drape, 3M Tegaderm® drape, acrylic drape such as one available from Avery Dennison, or an incise drape.

The reduced-pressure bridge 308 has a first end 320 and a second end 322. A first encapsulating member 324 is coupled to a second encapsulating member 326 to form an encapsulating envelope 328. The first encapsulating envelope 328 encloses, at least in part, a delivery manifold 330. The second encapsulating member 326 has a second aperture 332 proximate the first end 320. The second aperture 332 is sized and configured to align with the first aperture 318. A reduced-pressure interface 334 is fluidly coupled at a reduced-pressure-interface site 336. The reduced-pressure interface 334 is fluidly coupled to a third aperture 338. A reduced-pressure delivery conduit 340 fluidly couples a reduced-pressure source (not shown) to the reduced-pressure interface 334. A moisture-removing device 342 is coupled to the patient-facing side of the encapsulating envelope 328 and in particular to the second encapsulating member 326.

Referring now to FIG. 6, a schematic diagram of an illustrative embodiment of a reduced-pressure treatment kit 400 for use with limited-access tissue sites is presented. The reduced-pressure treatment kit 400 facilitates organized and efficient application of reduced pressure to a tissue site and particularly to a limited-access tissue site. The reduced-pressure treatment kit 400 may include a sealed package or container that is opened by a healthcare provider. The reduced-pressure treatment kit 400 may include a reduced-pressure bridge 402, a reduced-pressure interface 404, a reduced-pressure delivery conduit 408, a ruler 416, a manifold unit 418, and a perforated sealing sheet 420, or any combination thereof. The ruler 416 may be used to help size the dimensions of the wound and may provide other information to help assess a wound.

The reduced-pressure bridge 402 may be analogous the reduced-pressure bridges 102, 200, and 308 previously presented. The reduced-pressure bridge 402 has a first end 403 and a second end 405. A reduced-pressure interface 404 may be coupled to a reduced-pressure-interface site 406 on the reduced-pressure bridge 402. The reduced-pressure delivery conduit 408 may be coupled to the reduced-pressure interface 404. The reduced-pressure delivery conduit 408 may include a visual indicia flag or label 410 and restricting clip or clamp 412. A fitting 414 may be coupled at one end of the reduced-pressure delivery conduit 408 to facilitate coupling to a reduced-pressure source (not shown). That the reduced-pressure bridge 402 is already encapsulated as provided in the reduced-pressure treatment kit 400 allows for easy application and requires minimal work to deploy the reduced-pressure bridge 402.

The perforated sealing sheet 420 has adhesive on a patient-facing side and has a releasable backing or release liner that covers the adhesive until it is ready for application. A plurality of perforations, e.g., mid-line perforation 422, provides a location where the healthcare provider may readily tear the perforated sealing sheet 420 to form new members. Thus, for example, a portion of the mid-line perforation 422, a first longitudinal perforation 424, and a portion of an end perforation 426 may be torn to form a first sealing member 428, which has an aperture 430. The sealing member 428 may be used to secure a treatment manifold in place. Other longitudinal perforations 432 may be torn to form securing strips 434 that are used to hold the reduced-pressure bridge 402 in place as will be described further below.

Figure 7A:
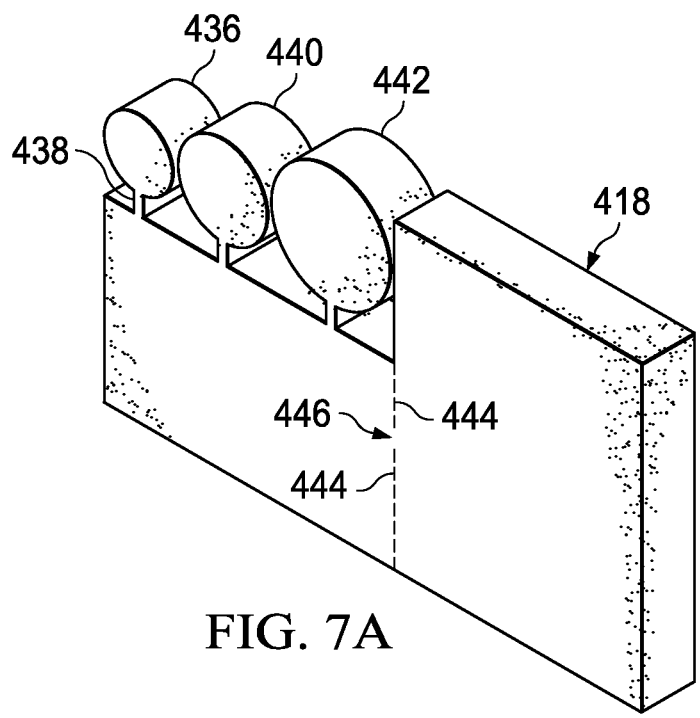
FIG. 7A is a schematic, perspective view of an illustrative manifold unit.
Figure 7B:
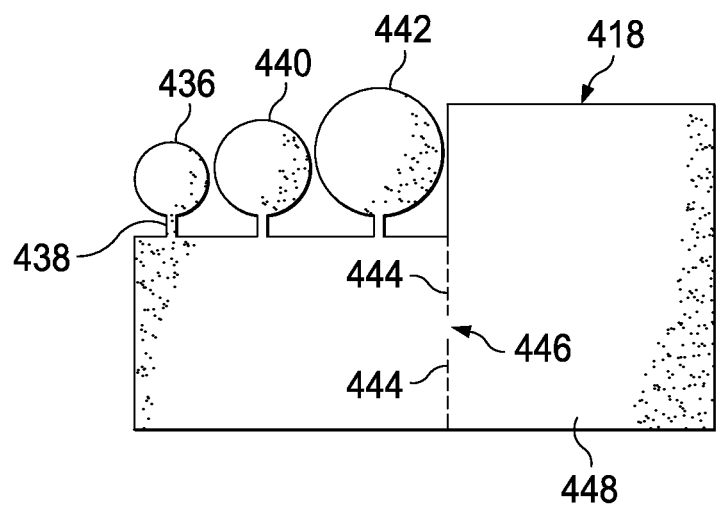
FIG. 7B is a schematic plan view of the manifold unit of FIG. 7A.

The illustrative manifold unit 418, which is also shown in FIGS. 7A and 7B, is made of a manifold material. For example, the manifold unit 418 may be formed from a reticulated foam, such as a Granufoam® material from Kinetic Concepts, Inc. of San Antonio, Tex. The manifold unit 418 has a number of pre-cut manifold components that may be used. For example, a first treatment manifold 436 is formed and has a connection stem 438 that be readily torn. Numerous additional treatment manifolds, e.g., second treatment manifold 440 and third treatment manifold 442, may be included. A mid-portion of the manifold unit 418 may have a precut 444, which is cut all the way through except for a small tag or portion 446 used to hold the manifold unit 418 together until torn. When the stems, e.g., stem 438, are torn and the tag 446 is torn, two manifold blocks 448 and 450 are formed.

Referring now primarily to FIGS. 5 and 6, an illustrative deployment of a reduced-pressure treatment system, such as the reduced-pressure treatment system 300, will be described. The wound or tissue site (e.g., tissue site 302 in FIG. 5) may first be prepared, such by removal of any other dressings and debriding the wound and the peri-wound area. The wound or tissue may be assessed with respect to size and condition.

The perforations, e.g., midline perforation 422, on the perforated sealing sheet 420 are torn. Tearing the perforations produces the sealing member 428, which has aperture 430, a plurality of securing strips 434, and an additional sealing member 429.

A treatment manifold (e.g., treatment manifold 310 in FIG. 5) is placed proximate the tissue site, e.g., a wound. Depending on the size, the healthcare provider may tear off the first treatment manifold 436, second treatment manifold, 440, or third treatment manifold 442 from the manifold unit 418 in the reduced-pressure treatment kit 400. If the size is notably different, a custom treatment manifold may be cut from one of the manifold blocks 448, 450. The properly sized treatment manifold is placed proximate the tissue site. If more than one treatment manifold is used, the number may be recorded on the visual indicia flag 410. Then, the sealing member 428 is attached over the wound or tissue site 302 with the aperture 430 centered thereon. The sealing member 428 may first need to be trimmed to an appropriate size, which in one embodiment provides a 3-5 mm border around the tissue site. To attach the sealing member 428, the release liner may be removed and the adhesive placed against a portion of intact epidermis; this is analogous to the attachment device 314 being used to attach the sealing member 312 to the epidermis in FIG. 5. The reduced-pressure bridge, e.g., reduced-pressure bridge 402, is then installed.

A release liner (e.g., release liner 220 in FIG. 2B) is removed exposing an adhesive on the first end 403 of the reduced-pressure bridge 402, and an aperture (e.g., aperture 213 in FIG. 2B) on the reduced-pressure bridge 402 is substantially aligned with the aperture 430 on the sealing member 428 (e.g., sealing member 312 in FIG. 5) and then the first end 403 pressed against the sealing member 428. The second end 405 of the reduced-pressure bridge 402 is placed at a convenient location and the securing strips 434 are used to secure the reduced-pressure bridge 402 in the desired location and at a point in between as desired. If the reduced-pressure bridge 402 is longer than desired, a fold shaped like a "Z" may be added into the reduced-pressure bridge 402 to shorten the effective length.

A reduced-pressure source (e.g., reduced-pressure source 120 in FIG. 1) may then be provided and the fitting 414 on the reduced-pressure delivery conduit 408 coupled to the reduced-pressure source or to another conduit supplying reduced pressure. The reduced-pressure source may then be activated.

Although the present invention and its advantages have been disclosed in the context of certain illustrative, non-limiting embodiments, it should be understood that various changes, substitutions, permutations, and alterations can be made without departing from the scope of the invention as defined by the appended claims.

I claim:

1. A reduced-pressure bridge for treating a tissue site, comprising:
   a delivery manifold;
   an encapsulating envelope at least partially enclosing the delivery manifold and having a patient-facing side;
   an interface site formed at a second end of the reduced-pressure bridge, wherein the second end is adapted to be positioned at a remote location from the tissue site;
   an aperture formed at a first end of the reduced-pressure bridge on the patient-facing side of the encapsulating envelope, wherein the first end of the reduced-pressure bridge is located at an opposite end of the reduced-pressure bridge from the second end of the reduced-pressure bridge, and wherein the delivery manifold is configured to communicate reduced pressure from the interface site at the second end of the reduced-pressure bridge along a length of the patient-facing side and through the aperture at the first end of the reduced-pressure bridge to a treatment manifold external to the reduced-pressure bridge; and
   an adhesive on the first end for fluidly coupling the reduced-pressure bridge to the treatment manifold proximate to the tissue site.

2. The reduced-pressure bridge of claim 1, further comprising a moisture-removing device on at least a portion of the encapsulating envelope, wherein the moisture-removing device comprises a wicking material on the patient-facing side of the encapsulating envelope, and wherein the wicking material is adapted to contact a remote tissue portion and to absorb liquid from the remote tissue portion.

3. The reduced-pressure bridge of claim 2, wherein the wicking material comprises a cloth-material drape.

4. The reduced-pressure bridge of claim 2, wherein the wicking material comprises a non-woven fabric.

5. The reduced-pressure bridge of claim 2, wherein the wicking material covers at least 50 percent of the patient-facing side of the encapsulating envelope.

6. The reduced-pressure bridge of claim 2, wherein the wicking material covers at least 70 percent of the patient-facing side of the encapsulating envelope.

7. The reduced-pressure bridge of claim 2, wherein the wicking material covers at least 80 percent of the patient-facing side of the encapsulating envelope.

8. The reduced-pressure bridge of claim 2, wherein the wicking material extends along a length of the encapsulating envelope.

9. The reduced-pressure bridge of claim 1, wherein the reduced-pressure bridge has a length (L), and wherein L>120 mm.

10. The reduced-pressure bridge of claim 1, wherein the encapsulating envelope comprises:
a first encapsulating member having a first perimeter portion;
a second encapsulating member having a second perimeter portion; and
wherein the first perimeter portion is coupled to the second perimeter portion such that the delivery manifold is at least partially enclosed by the first encapsulating member and the second encapsulating member.

11. The reduced-pressure bridge of claim 10, wherein the first encapsulating member and the second encapsulating member comprise a polyurethane material.

12. The reduced-pressure bridge of claim 1, further comprising a moisture-removing device on at least a portion of the encapsulating envelope, wherein the moisture-removing device comprises a comfort manifold and another encapsulating member for encapsulating at least a portion of the comfort manifold on the patient-facing side, and wherein the other encapsulating member has a plurality of apertures.

13. The reduced-pressure bridge of claim 1, wherein the reduced-pressure bridge has a length (L), and wherein L>200 mm.

14. The reduced-pressure bridge of claim 1, wherein the reduced-pressure bridge has a length (L), and a width (W) and wherein L>(4*W).

15. The reduced-pressure bridge of claim 1, wherein the delivery manifold is a foam material.

16. The reduced-pressure bridge of claim 1, wherein the delivery manifold is configured to transfer reduced pressure from the remote location to the tissue site.

17. The reduced-pressure bridge of claim 1, wherein reduced pressure is transferable to the tissue site through the aperture.

18. The reduced-pressure bridge of claim 1, wherein the delivery manifold is configured to distribute fluids to the tissue site.

19. The reduced-pressure bridge of claim 1, wherein the reduced-pressure bridge is configured to distribute fluids to the tissue site.

20. The reduced-pressure bridge of claim 1, wherein the patient-facing side of the encapsulating envelope is a second side of the reduced-pressure bridge, and wherein the interface site is formed on a first side of the reduced-pressure bridge.

21. The reduced-pressure bridge of claim 1, wherein the adhesive is positioned about the aperture on the first end of the reduced-pressure bridge.

22. The reduced-pressure bridge of claim 1, wherein the reduced-pressure bridge comprises a length adapted to extend from the tissue site to the remote location.

23. The reduced-pressure bridge of claim 1, wherein the reduced-pressure bridge is configured to extend along a tissue surface away from the tissue site to the remote location.

24. The reduced-pressure bridge of claim 1, wherein the reduced-pressure bridge is configured to maintain contact along a tissue surface away from the tissue site to the remote location.

25. The reduced-pressure bridge of claim 1, wherein the second end is adapted to be in direct contact with the remote location.

26. The reduced-pressure bridge of claim 1, wherein the first end is adapted to be disposed at a position over the tissue site, and wherein the second end is adapted to be disposed at a position that is not over the tissue site.

27. The reduced-pressure bridge of claim 1, wherein the treatment manifold is adapted to be positioned at the tissue site and between the tissue site and the aperture at the first end of the reduced-pressure bridge.

* * * * *